(12) United States Patent
Cui et al.

(10) Patent No.: US 9,474,645 B2
(45) Date of Patent: Oct. 25, 2016

(54) PUNCTAL PLUGS FOR THE DELIVERY OF ACTIVE AGENTS

(75) Inventors: Han Cui, Basking Ridge, NJ (US); Zhigang Li, Hillsborough, NJ (US); Edgar V. Menezes, Jacksonville, FL (US); Aruna Nathan, Bridgewater, NJ (US); Michael J. Trezza, II, Great Meadows, NJ (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 778 days.

(21) Appl. No.: 11/759,269

(22) Filed: Jun. 7, 2007

(65) Prior Publication Data

US 2007/0299516 A1    Dec. 27, 2007

Related U.S. Application Data

(60) Provisional application No. 60/805,383, filed on Jun. 21, 2006.

(51) Int. Cl.
*A61F 2/00* (2006.01)
*A61F 13/00* (2006.01)
*A61F 2/14* (2006.01)
*A61F 9/00* (2006.01)
*A61F 9/007* (2006.01)
*A61K 9/00* (2006.01)

(52) U.S. Cl.
CPC ......... *A61F 9/0017* (2013.01); *A61F 9/00772* (2013.01); *A61K 9/0051* (2013.01)

(58) Field of Classification Search
None
See application file for complete search history.

(56) References Cited

U.S. PATENT DOCUMENTS

| 3,949,750 | A | 4/1976 | Freeman |
| 5,773,021 | A | 6/1998 | Gurtler et al. |
| 5,962,548 | A | 10/1999 | Vanderlaan et al. |
| 6,016,806 | A * | 1/2000 | Webb ............... A61B 17/12022 128/846 |
| 6,020,445 | A | 2/2000 | Vanderlaan et al. |
| 6,099,852 | A | 8/2000 | Jen |
| 6,196,993 | B1 * | 3/2001 | Cohan et al. ............. 604/891.1 |
| 6,238,363 | B1 | 5/2001 | Kurihashi |
| 6,367,929 | B1 | 4/2002 | Maiden et al. |
| 6,375,972 | B1 | 4/2002 | Guo et al. |
| 6,383,192 | B1 | 5/2002 | Kurihashi |
| 6,490,548 | B1 | 12/2002 | Engel |
| 6,822,016 | B2 | 11/2004 | McCabe et al. |
| 6,916,483 | B2 * | 7/2005 | Ralph et al. ................. 424/422 |
| 6,923,800 | B2 | 8/2005 | Chen et al. |
| 7,008,396 | B1 * | 3/2006 | Straub ............................. 604/8 |

(Continued)

FOREIGN PATENT DOCUMENTS

| JP | 11-047183 | 2/1999 |
| JP | 61115559 A | 12/2002 |

(Continued)

OTHER PUBLICATIONS

Sheath. (2001). In Chambers 21st Century Dictionary. Retrieved from http://www.credoreference.com/entry/chambdict/sheath.*

(Continued)

*Primary Examiner* — Robert A Wax
*Assistant Examiner* — Randeep Singh

(57) ABSTRACT

The invention provides punctal plugs for the delivery of active agent to one or both of the tear fluid of the eye and to the nasolacrimal duct that comprise a body, at least one cap, and optionally a collarette.

2 Claims, 9 Drawing Sheets

(56) References Cited

U.S. PATENT DOCUMENTS

| | | | |
|---|---|---|---|
| 7,727,954 B2 * | 6/2010 | McKay | 514/2 |
| 2002/0110592 A1 | 8/2002 | Brubaker et al. | |
| 2003/0143280 A1 | 7/2003 | El-Sherif et al. | |
| 2004/0013704 A1 | 1/2004 | Kabra et al. | |
| 2004/0039399 A1 | 2/2004 | Norrby et al. | |
| 2004/0068215 A1 * | 4/2004 | Adelson et al. | 602/26 |
| 2004/0092911 A1 | 5/2004 | Yaacobi | |
| 2004/0175410 A1 | 9/2004 | Ashton et al. | |
| 2004/0208910 A1 | 10/2004 | Ashton et al. | |
| 2005/0019371 A1 * | 1/2005 | Anderson et al. | 424/426 |
| 2005/0163844 A1 | 7/2005 | Ashton et al. | |
| 2005/0197614 A1 | 9/2005 | Pritchard et al. | |
| 2005/0220882 A1 | 10/2005 | Pritchard et al. | |
| 2005/0232972 A1 | 10/2005 | Odrich | |
| 2006/0013835 A1 | 1/2006 | Anderson et al. | |
| 2006/0020248 A1 | 1/2006 | Prescott | |
| 2006/0020253 A1 | 1/2006 | Prescott | |
| 2006/0110429 A1 | 5/2006 | Reiff et al. | |
| 2007/0243230 A1 * | 10/2007 | de Juan et al. | 424/427 |

FOREIGN PATENT DOCUMENTS

| | | |
|---|---|---|
| JP | 2004018472 | 1/2004 |
| WO | WO 00/62760 | 10/2000 |
| WO | WO 00/62760 A1 | 10/2000 |
| WO | WO 2004/066980 A2 | 8/2004 |
| WO | WO 2005/086694 A2 | 9/2005 |
| WO | WO 2006/014434 A2 | 2/2006 |
| WO | WO 2006/014793 A1 | 2/2006 |
| WO | WO 2006014793 | 2/2006 |
| WO | WO 2006/031658 A2 | 3/2006 |
| WO | WO 2006032089 A1 | 3/2006 |

OTHER PUBLICATIONS

Mullner et al. British Journal of Ophthalmology 199 83:949-952.*
U.S. Appl. No. 60/805,380, Johnson & Johnson Vision Care, Inc.
Serial No. Unassigned, Johnson & Johnson Vision Care, Inc.
U.S. Appl. No. 60/805,378, Johnson & Johnson Vision Care, Inc.
Reasons for Rejection from the Japanese Patent Office dated Feb. 5, 2013, for Japanese Patent Application No. 2009-516644.
Search Report for corresponding Taiwan Patent Application No. 09122151 dated Jan. 21, 2013.
Written Opinion issued by the Singapore Patent Office for Application No. 201106704-8 dated Sep. 24, 2014.
Notification of Reasons for Refusal dated May 8, 2012 cited in corresponding Japanese Patent Application No. JP2007-162970.

* cited by examiner

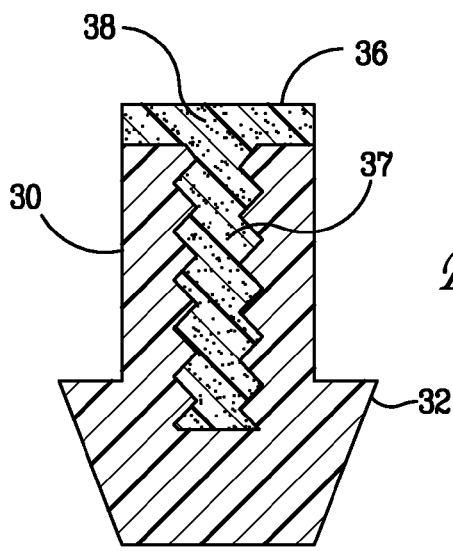
*FIG. 3A*
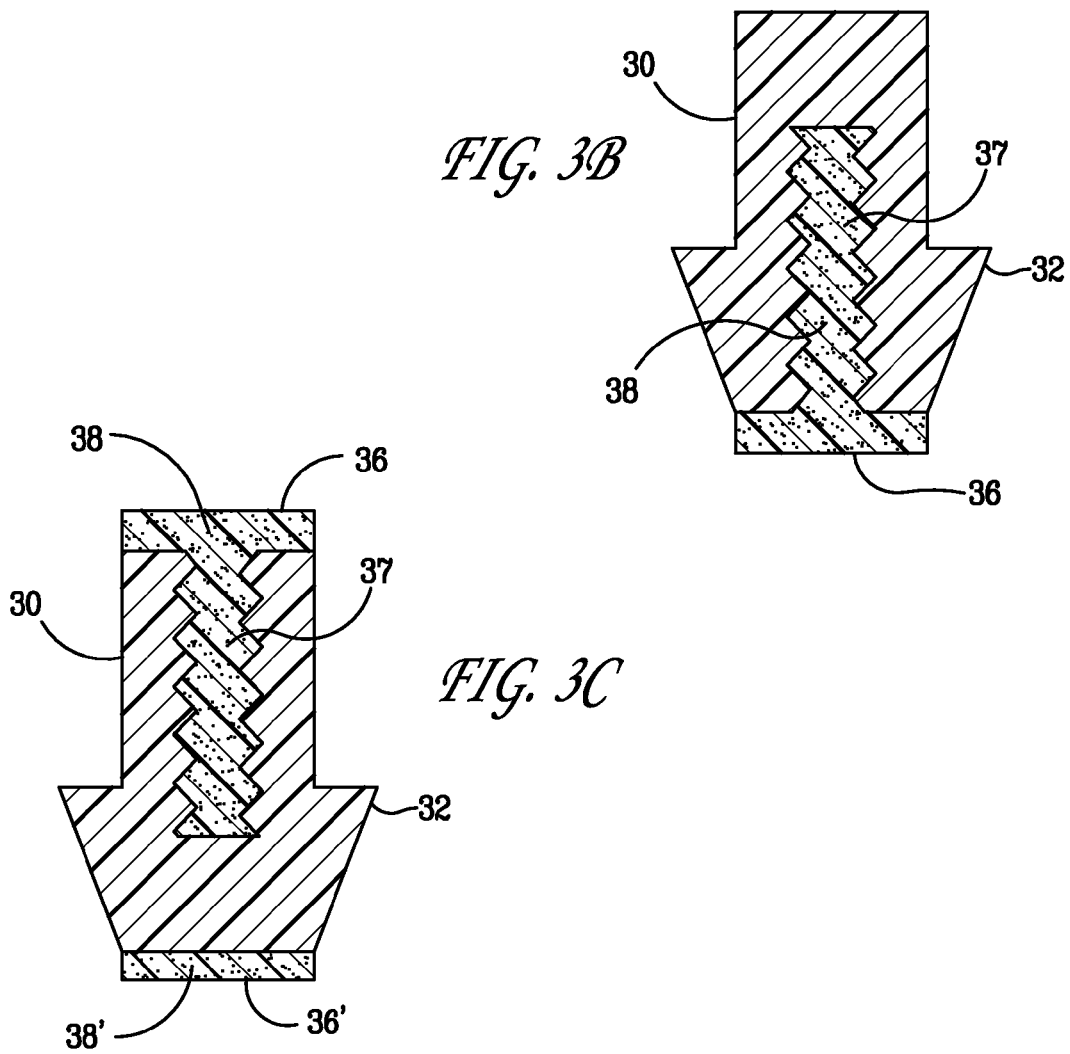
*FIG. 3B*
*FIG. 3C*

PUNCTAL PLUGS FOR THE DELIVERY OF ACTIVE AGENTS

RELATED APPLICATIONS

This application claims priority from provisional application U.S. Ser. No. 60/805,383 filed on Jun. 21, 2006.

FIELD OF THE INVENTION

The present invention relates to devices suitable for delivering substances to one or more of the eye, nose and throat. In particular, the invention relates to punctal plugs for delivery of at least one active agent.

BACKGROUND OF THE INVENTION

Human tears are secreted by the lacrimal gland and flow across the surface of the eye to a shallow pool, known as the lacrimal lake, located where the eyelids come together at their inner ends. From there, the tears drain through small openings in each of the eyelids, termed the superior lacrimal punctum and the inferior lacrimal punctum. From the superior and inferior puncta, the tears pass into the superior and inferior lacrimal canaliculus, respectively, which are duct-like pathways that lead to the lacrimal sac. The lacrimal sac is the superior, expanded portion of the nasolacrimal duct, which drains tears into the nasal system. Active agents can thus be delivered to the nose and throat through the lacrimal canaliculi, which lead into the nasolacrimal duct.

Active agents frequently are administered to the eye for the treatment of ocular diseases and disorders. Conventional means for delivering active agents to the eye involve topical application to the surface of the eye. The eye is uniquely suited to topical administration because, when properly constituted, topically applied active agents can penetrate through the cornea and rise to therapeutic concentration levels inside the eye. Active agents for ocular diseases and disorders may be administered orally or by injection, but such administration routes are disadvantageous in that, in oral administration, the active agent may reach the eye in too low a concentration to have the desired pharmacological effect and their use is complicated by significant, systemic side effects, while injections pose the risk of infection.

The majority of ocular active agents are currently delivered topically using eye drops which, though effective for some applications, are inefficient. When a drop of liquid is added to the eye, it overfills the conjunctival sac, the pocket between the eye and the lids, causing a substantial portion of the drop to be lost due to overflow of the lid margin onto the cheek. In addition, a substantial portion of the drop that remains on the ocular surface is drained into the lacrimal puncta, diluting the concentration of the drug.

BRIEF DESCRIPTION OF THE DRAWINGS

FIG. 3A is a sectional view of a punctal plug having a body 30 with an enlarged segment 32 and a cap 36 that includes stem 37 and contains active agent 38. The stem portion 37 of the cap is screwed into the body 30 of the punctal plug.

FIG. 3B is a sectional view of a punctal plug having a body 30 with an enlarged segment 32 and a cap 36 that includes stem 37 and contains active agent 38. The stem portion 37 of the cap is screwed into the body 30 of the punctal plug.

FIG. 3C is a sectional view of a punctal plug having a body 30 with an enlarged segment 32 a first cap 36 that includes stem 37 and contains active agent 38, and a second cap 36' that includes active agent 38'. The stem portion 37 of the first cap is screwed into the body 30 of the punctal plug.

DETAILED DESCRIPTION OF THE INVENTION AND ILLUSTRATIVE EMBODIMENTS

The present invention provides punctal plugs that can be used to deliver active agents to one or both of the nasolacrimal duct and to the tear fluid of the eye. The punctal plugs comprise, consist essentially of, and consist of: (a) a body having a first end, a second end, and a lateral surface extending between the two ends; and (b) a cap adjacent to the first end of the body, a cap adjacent to the second end of the body, or caps adjacent to both the first and second ends of the body, wherein the caps are comprised of an active agent-containing material that contains at least one active agent.

Figure 1A:
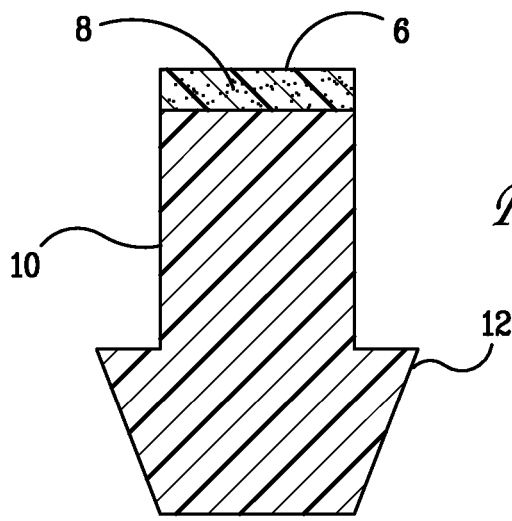
FIG. 1A is a sectional view of a punctal plug having a body 10 with an enlarged segment 12 and a cap 6 that contains active agent 8.
Figure 1B:
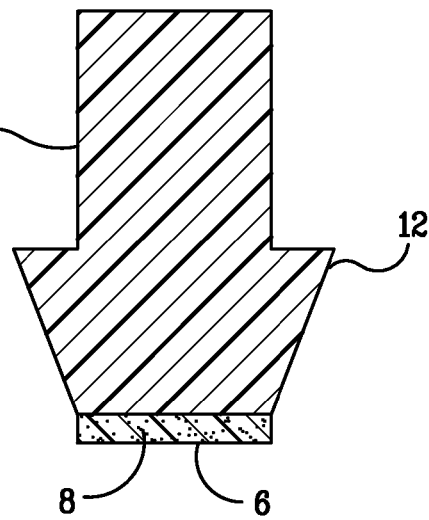
FIG. 1B is a sectional view of a punctal plug having a body 10 with an enlarged segment 12 and a cap 6 that contains active agent 8.
Figure 1C:
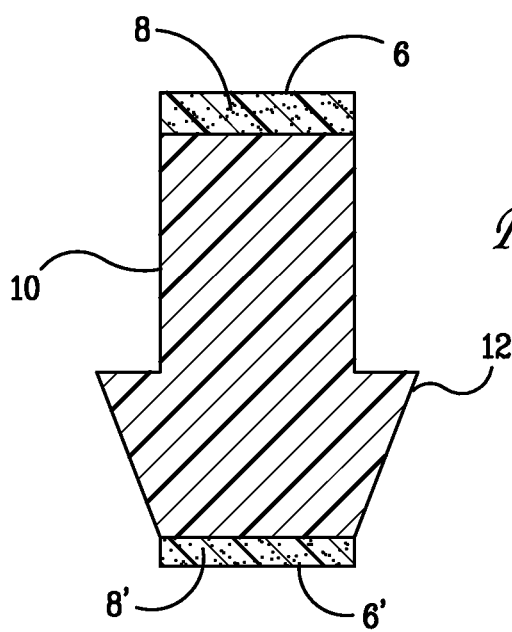
FIG. 1C is a sectional view of a punctal plug having a body 10 with an enlarged segment 12, a first cap 6 that contains active agent 8, and a second cap 6' that contains active agent 8'.
Figure 2A:
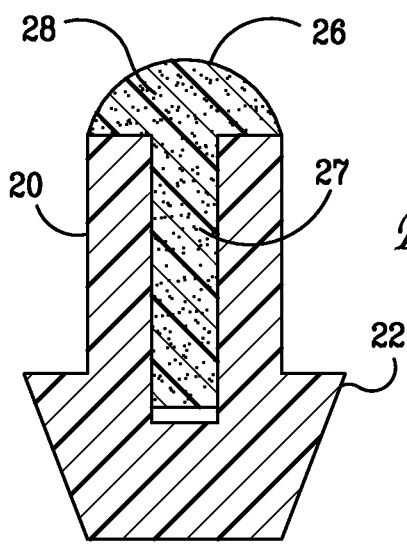
FIG. 2A is a sectional view of a punctal plug having a body 20 with an enlarged segment 22 and a cap 26 that includes a stem 27 and contains active agent 28. The stem portion of the cap 27 is positioned within the body of the punctal plug 20.
Figure 2B:
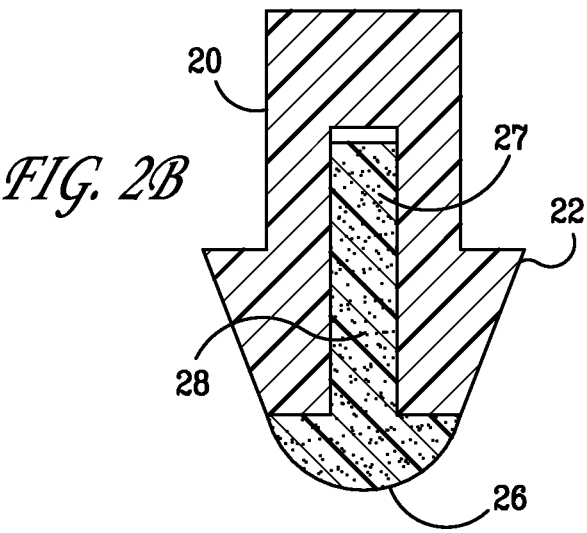
FIG. 2B is a sectional view of a punctal plug having a body 20 with an enlarged segment 22 and a cap 26 that includes a stem 27 and contains active agent 28. The stem portion of the cap 27 is positioned within the body 20 of the punctal plug.
Figure 2C:
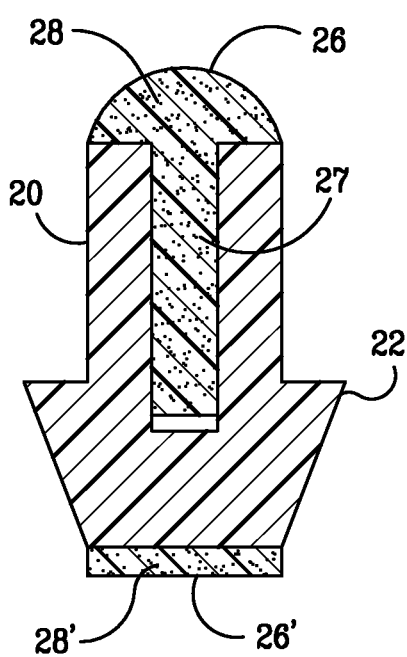
FIG. 2C is a sectional view of a punctal plug having a body 20 with an enlarged segment 22, a first cap 26 that includes a stem 27 and contains active agent 28, and a second cap 26' that contains active agent 28'. The stem portion of the first cap 27 is positioned within the body 20 of the punctal plug.

In FIGS. 1A-C and 2A-C are depicted embodiments of the punctal plugs of the present invention with bodies 10 and 20. The active agent, shown as 8, 8', 28, and 28' in the figures, is released from the caps 6 and 26, respectively, for example, when the caps dissolve or degrade, or the active agent simply diffuses from the caps, depending upon the an active agent-containing material material from which the caps are made. The caps can adhere to an end of the bodies. Alternatively, as depicted in FIGS. 2A-C, the caps 26 may have a stem portion 27 that extends into the body 20 of the plug.

Figure 4A:
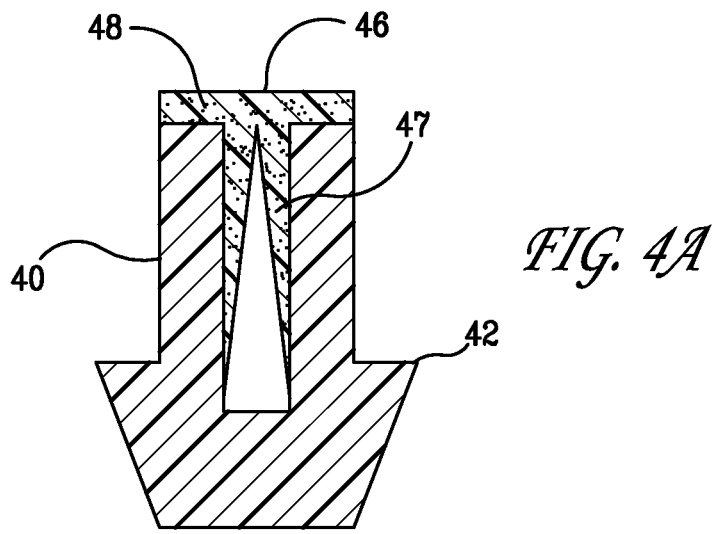
FIG. 4A is a sectional view of a punctal plug having a body 40 with an enlarged segment 42 and a cap 46 that includes a stem 47 and contains active agent 48. The stem portion 47 of the cap is clipped into the body 40 of the punctal plug.
Figure 4B:
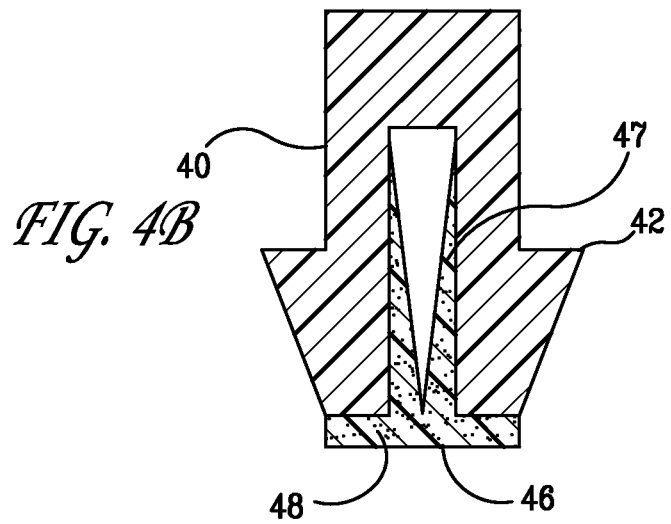
FIG. 4B is a sectional view of a punctal plug having a body 40 with an enlarged segment 42 and a cap 46 that includes a stem 47 and contains active agent 48. The stem portion 47 of the cap is clipped into the body 40 of the punctal plug.
Figure 4C:
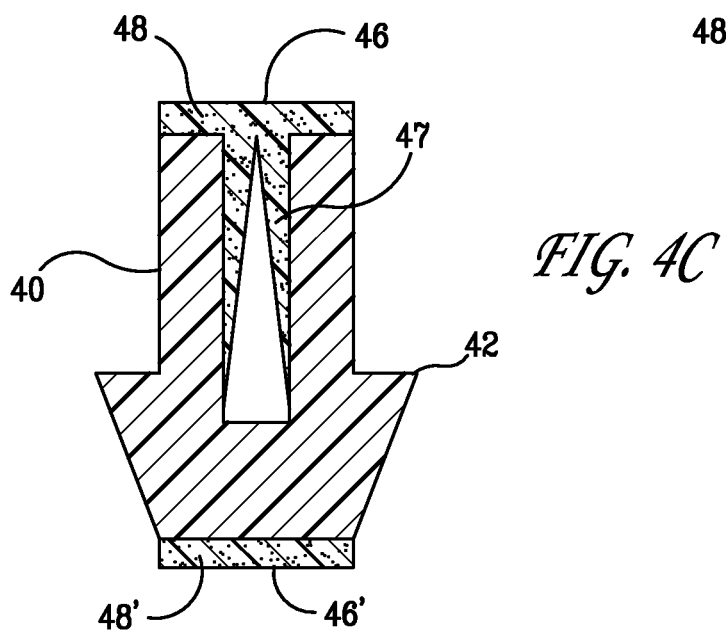
FIG. 4C is a sectional view of a punctal plug having a body 40 with an enlarged segment 42 a first cap 46 that includes stem 47 and contains active agent 48, and a second cap 46' that includes active agent 48'. The stem portion 47 of the first cap is clipped into the body 40 of the punctal plug.
Figure 5A:
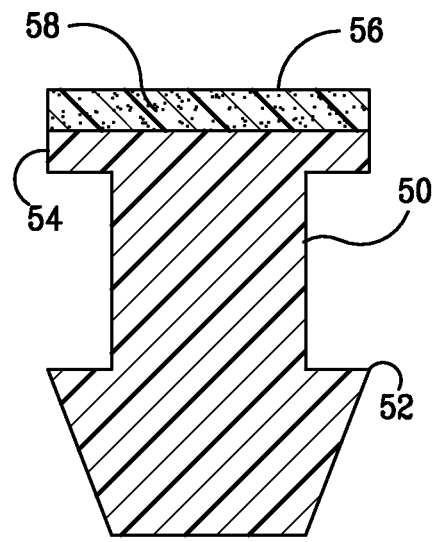
FIG. 5A is a sectional view of a punctal plug having a body 50 with an enlarged segment 52, a collarette 54, and a cap 56 that contains active agent 58.
Figure 9A:
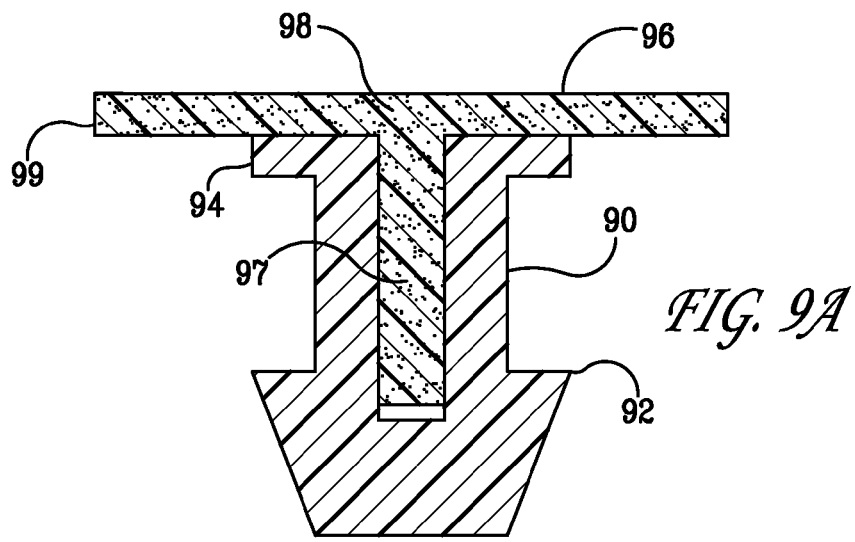
FIG. 9A is a sectional view of a punctal plug having a body 90 with an enlarged segment 92, a collarette 94, and a cap 96 that includes a stem 97 and contains active agent 98. The stem portion 97 of the cap is positioned within the body 90 of the punctal plug, and a portion 99 of the cap extends beyond the collarette 94.
Figure 9B:
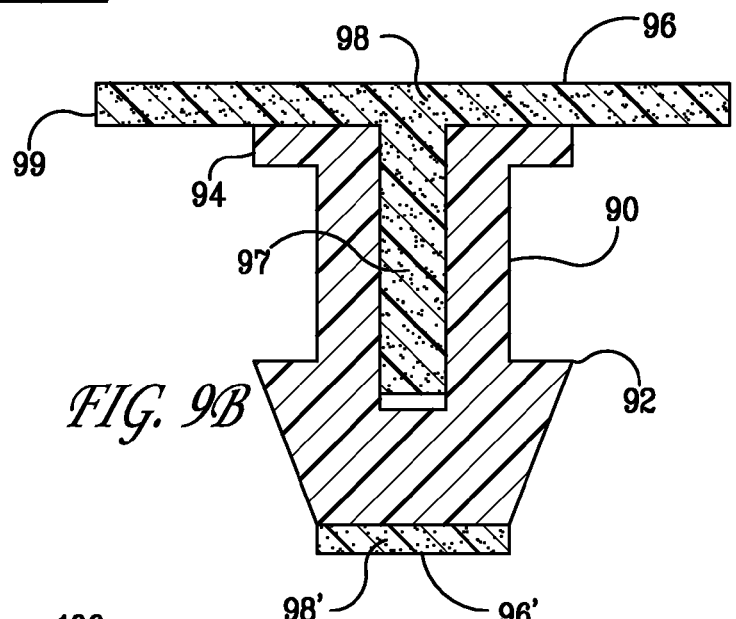
FIG. 9B is a sectional view of a punctal plug having a body 90 with an enlarged segment 92, a collarette 94, a first cap 96 that includes a stem 97 and contains active agent 98, and a second cap 96' that includes active agent 98'. The stem portion 97 of the first cap is positioned within the body 90 of the punctal plug, and a portion 99 of the first cap extends beyond the collarette 94.

In another embodiment and as shown in FIGS. 3A-C, the stem portion may be screwed therein. As yet another alternative and as shown in FIGS. 4A-C, the stem may be clipped be into the body. As still another alternative and as shown in FIGS. 5A and B, the punctal plugs may have a collarette at the first end of the body. When such punctal plugs are inserted into the lacrimal canaliculus, the collarette preferably rests on the exterior of the lacrimal punctum and at least a portion of the cap is adjacent to the collarette. As shown in FIGS. 9A and B, particular punctal plugs having collarettes 94 may have caps 99 that are made of a flexible material, and at least a portion of the cap of such punctal plugs is elongated and extends beyond the collarette, thereby increasing the amount of active agent 98 that the cap can contain.

Figure 5B:
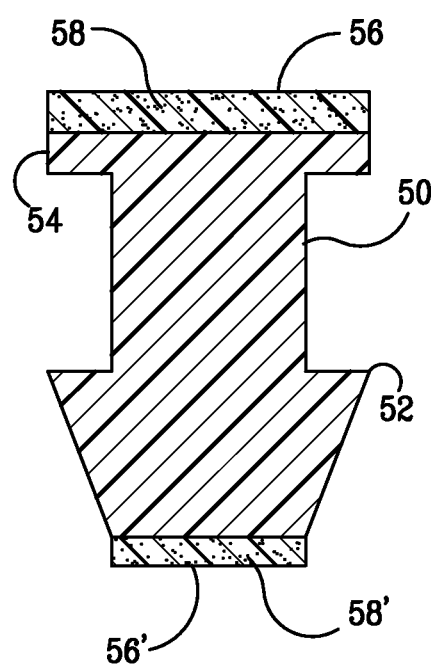
FIG. 5B is a sectional view of a punctal plug having a body 50 with an enlarged segment 52, a collarette 54, a first cap 56 that contains active agent 58, and a second cap 56' that contains active agent 58'.
Figure 6A:
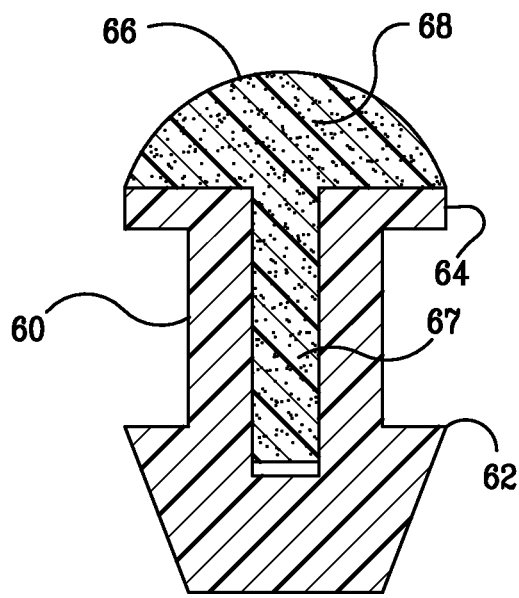
FIG. 6A is a sectional view of a punctal plug having a body 60 with an enlarged segment 62, a collarette 64, and a cap 66 that includes a stem 67 and contains active agent 68. The stem portion 67 of the cap is positioned within the body 60 of the punctal plug.
Figure 6B:
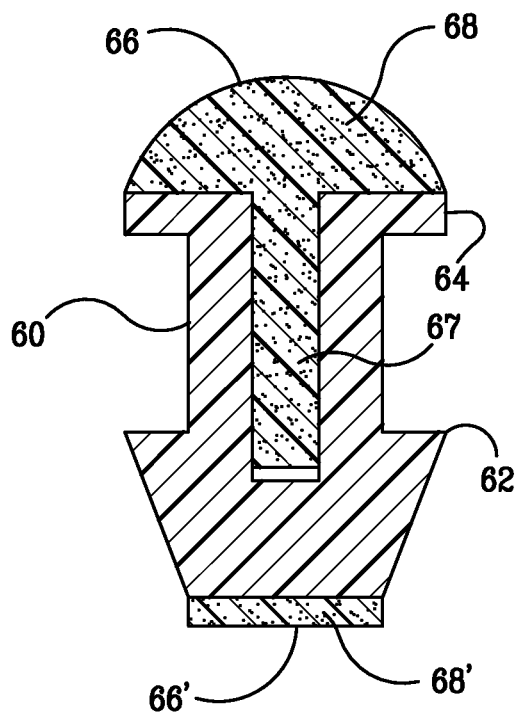
FIG. 6B is a sectional view of a punctal plug having a body 60 with an enlarged segment 62, a collarette 64, a first cap 66 that includes a stem 67 and contains active agent 68, and a second cap 66' that includes active agent 68'. The stem portion 67 of the first cap is positioned within the body 60 of the punctal plug.
Figure 7A:
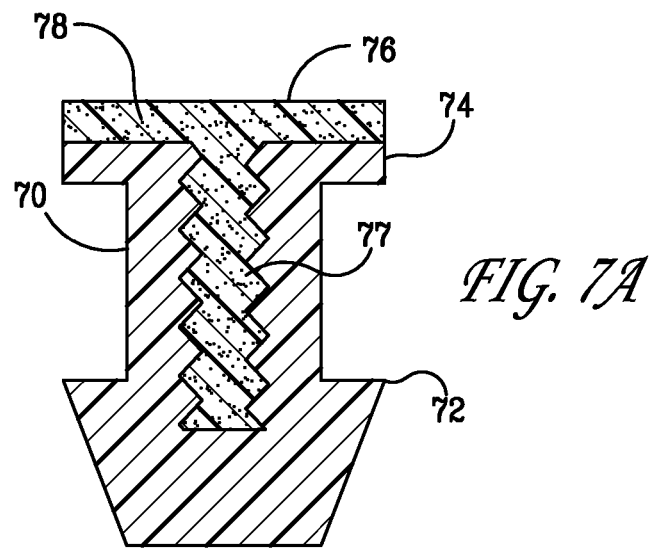
FIG. 7A is a sectional view of a punctal plug having a body 70 with an enlarged segment 72, a collarette 74, and a cap 76 that includes a stem 77 and contains active agent 78. The stem portion 77 of the cap is screwed into the body 70 of the punctal plug.
Figure 7B:
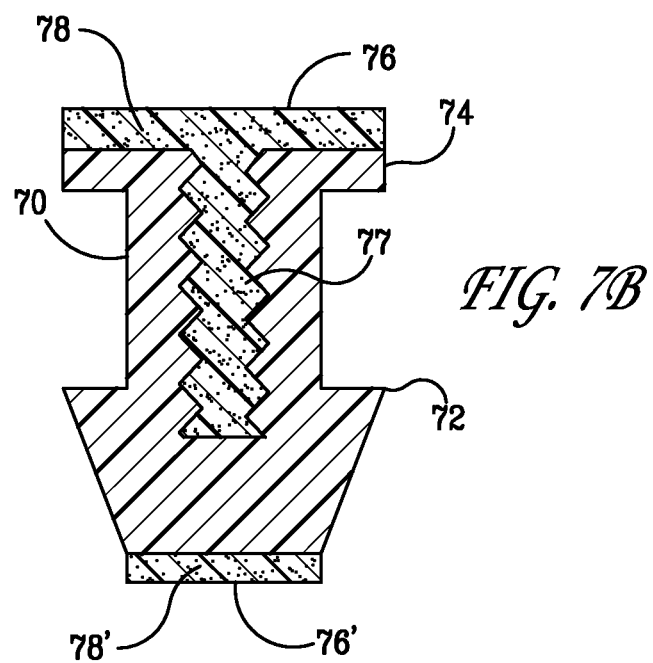
FIG. 7B is a sectional view of a punctal plug having a body 70 with an enlarged segment 72, a collarette 74, a first cap 76 that includes a stem 77 and contains active agent 78, and a second cap 76' that includes active agent 78'. The stem portion 77 of the first cap is screwed into the body 70 of the punctal plug.
Figure 8A:
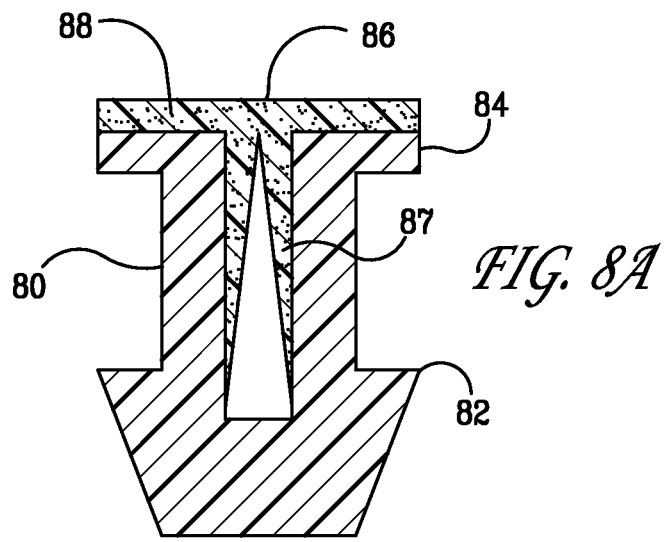
FIG. 8A is a sectional view of a punctal plug having a body 80 with an enlarged segment 82, a collarette 84, and a cap 86 that includes a stem 87 and contains a active agent. The stem portion 87 of the cap is clipped into the body 80 of the punctal plug.
Figure 8B:
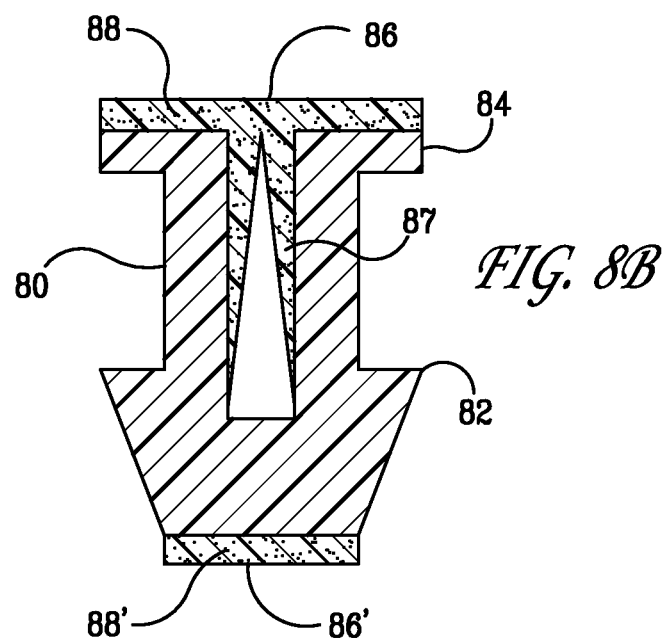
FIG. 8B is a sectional view of a punctal plug having a body 80 with an enlarged segment 82, a collarette 84, a first cap 86 that includes a stem 87 and contains active agent 88, and a second cap 86' that includes active agent 88'. The stem portion 87 of the first cap is clipped into the body 80 of the punctal plug.

For delivery of active agent into the tear fluid of the eye, when a punctal plug is inserted into the lacrimal canaliculus, preferably a cap is located adjacent to the end of the punctal plug that faces the eye, and the active agent is released into the tear fluid of the eye. For delivery of active agent into the nasolacrimal duct, when a punctal plug is inserted into the lacrimal canaliculus, preferably a cap is located adjacent to the end of the punctal plug that faces the nasolacrimal duct, and the active agent is released into the nasolacrimal duct. In particular embodiments of the invention, and as illustrated in FIGS. 1A-C for example, the body contains an enlarged segment 12 that secures the punctal plug in the lacrimal canaliculus. In further aspects of the invention and as depicted in FIGS. 2C and 5B for example, when a punctal plug is inserted into the lacrimal canaliculus, a cap is located adjacent to the end of the punctal plug that faces the eye, a second cap is located adjacent to the end of the punctal plug that faces the nasolacrimal duct, and the active agent may be released into both the tear fluid of the eye and the nasolacrimal duct.

As used herein, the term "punctal plug" refers to a device of a size and shape suitable for insertion into the inferior or superior lacrimal canaliculus of the eye through the inferior or superior lacrimal punctum.

As used herein, the term "active agent" refers to an agent capable of treating, inhibiting, or preventing a disorder or a disease. Exemplary active agents include, without limitation, pharmaceuticals and nutraceuticals. Preferred active agents are capable of treating, inhibiting, or preventing a disorder or a disease of one or more of the eye, nose and throat.

As used herein, the term "polymeric material" refers to a material made of one or more types of polymers that is capable of containing at least one active agent and releasing the active agent, for example, when the polymers dissolve or degrade, when the active agent diffuses from the polymers, or when a pro-drug is used in which the active agent is attached to the polymers and then released by being cleaved from the material.

As used herein, the phrase a "material that is at least partially water-soluble" refers to a material that exhibits a level of solubility in water sufficient to result in dissolution of the material upon exposure to an aqueous environment.

As used herein, the phrase a "material that is biodegradable" refers to a material that degrades to a detectable degree upon exposure to biologically active substances typically present in mammals.

As used herein, the phrase a "material that is insoluble in water" refers to a material that does not dissolve to a substantial degree upon exposure to water.

As used herein, the phrase a "material that is non-biodegradable" refers to a material that does not degrade to a substantial degree upon exposure to biologically active substances typically present in mammals.

As used herein, the phrases "cap is removable," "removable cap," and variations thereof, refer to caps of certain punctal plugs of the invention that can be removed from the punctal plugs before insertion, after insertion, or both of the punctal plugs into the lacrimal canaliculus, wherein removal of the cap does not affect the integrity of the remaining portion of the punctal plugs.

As used herein, "flexible material" refers to a material that is not rigid and that conforms to the surface of whatever object the material contacts.

The present invention encompasses numerous punctal plugs for the delivery of active agent to the tear fluid of the eye or to the nasolacrimal duct. The punctal plugs preferably are inserted into the inferior lacrimal canaliculus, the superior lacrimal canaliculus, or both the inferior and superior lacrimal canaliculi. If the punctal plugs are being used to deliver active agent to the tear fluid of the eye, the punctal plugs preferably have a collarette at one end of the body. The collarette is a portion of the punctal plug that extends radially outwardly from one end of the body to a degree sufficient so that at least a portion of the collarette will extend beyond and be exterior to the lacrimal punctum after insertion of the punctal plug into the lacrimal canaliculus. In FIG. 5A is depicted an example of a collarette 54. The portion of the punctal plugs without the collarette is inserted into one of the inferior lacrimal punctum or the superior lacrimal punctum, which are the openings of the lacrimal canaliculus on the margin of each eyelid. Referring to FIG. 5A, enlarged segment 52 and body 50 are inserted into one of the punctum, and the collarette rests against the exterior of the lacrimal punctum and keeps the punctal plug from slipping down into the lacrimal canaliculus, so that contact between the punctal plug and the tear fluid of the eye is maintained. The collarette can be of any size and shape sufficient to at least partially secure the punctal plug in the lacrimal punctum.

If the punctal plugs are being used to deliver active agent to the nasolacrimal duct, the punctal plugs preferably do not have a collarette so that they may be inserted at a sufficient depth within one or both of the lacrimal canaliculi such that the active agent is released into the lacrimal sac. In FIGS. 1B, 2B, and 3B are depicted examples of punctual plugs useful for delivery of an active agent to the nasal lacrimal duct.

The numerous punctal plugs of the invention each have various features and advantages. For example, certain punctal plugs have a body with a first end, a second end, and a lateral surface extending between the two ends. The lateral surface preferably has an outer diameter that is substantially circular in shape. A portion of the lateral surface of certain punctal plugs has an outer diameter that is greater than the outer diameter of the remainder of the lateral surface. With reference to FIG. 1A, the enlarged portion 12 of the lateral surface anchors or secures the punctal plugs in the lacrimal canaliculus. The enlarged portion can be any size or shape, and can be present on any part of the lateral surface, so long as the enlarged portion at least partially anchors the punctal plug in the lacrimal canaliculus. Conveniently, the enlarged portion may take the shape of an inverted triangle having a flattened apex.

The body of the punctal plugs may be made of any suitable biocompatible including, without limitation, silicone, silicone blends, silicone co-polymers, such as, for example, hydrophilic monomers of pHEMA (polyhydroxyethylmethacrylate), polyethylene glycol, polyvinylpyrrolidone, and glycerol, and silicone hydrogel polymers such as, for example, those described in U.S. Pat. Nos. 5,962,548, 6,020,445, 6,099,852, 6,367,929, and 6,822,016, incorporated herein in their entireties by reference. Other suitable biocompatible materials include, for example: poly(ethylene glycol); poly(ethylene oxide); poly(propylene glycol); poly (vinyl alcohol); poly(hydroxyethyl methacrylate); poly(vinylpyrrolidone); polyacrylic acid; poly(ethyloxazoline); poly(dimethyl acrylamide); phospholipids, such as, for example, phosphoryl choline derivatives; polysulfobetains; polysaccharides and carbohydrates, such as, for example, hyaluronic acid, dextran, hydroxyethyl cellulose, hydroxyl propyl cellulose, gellan gum, guar gum, heparan sulfate, chondritin sulfate, heparin, and alginate; proteins such as, for example, gelatin, collagen, albumin, and ovalbumin; polyamino acids; fluorinated polymers, such as, for example, polytetrafluoroethylene ("PTFE"), polyvinylidene fluoride ("PVDF"), and teflon; polypropylene; polyethylene; nylon; and ethylene vinyl alcohol ("EVA").

The punctal plugs of the invention have a cap, or a material or substance that covers a portion of the body. The caps can be of various shapes and sizes, but conveniently are of a size and shape suitable for being carried on or attached to one end of the punctual plug or a collarette. The caps are preferably adjacent to the first end of the body, the second end of the body, or both the first and second ends of the body. For those punctal plugs that have collarettes, a portion of the cap is preferably adjacent to the collarette.

The caps can adhere to the surface of a portion of the body, the collarette, or both the body and the collarette. The cap preferably adheres to the surface of an end of the either or both the body and the surface of the collarette. The cap can adhere to the surface of the body or collarette if the material that comprises the cap is itself adhesive. Such materials include, without limitation, cyanoacrylates and urethanes. Alternatively, a biocompatible adhesive can be used to adhere the cap to a portion of the surface of the body or collarette. Suitable biocompatible adhesives include, without limitation, silicones, polyurethanes, cyanoacrylates, polyacrylic acid, fibrin, and cross-linked proteins such as albumin and collagen-gelatin. Suitable agents that can be used for cross-linking include, without limitation, polyfunctional, homobifunctional or heterobifunctional cross-linkers such as bis N-succinimidyl-(pentaethylene glycol) esters. The adhesive can act via chemical reaction, or physical or mechanical interlock, and can be initiated via light, thermal or laser activation.

At least one active agent is disposed on, dispersed throughout, or otherwise contained within the cap of the punctal plugs, such that the cap serves as a carrier for the active agent. Depending upon the active agent-containing material from which the cap is made, the active agent can be released from the cap almost immediately, or the active agent can be released in a sustained manner over a desired period of time. The material may be any material that is compatible with the active agent or agents to be delivered by the plug and is capable of releasing the active agent in the desired manner, for example by dissolving or degrading of the material or diffusion of the active agent from the material. Any number of material may be used as the active agent-containing material including, without limitation, polymeric materials, both naturally occurring and synthetic, non-polymeric materials including, without limitation, glasses and clays, organic materials, inorganic materials including, without limitation, porous ceramics, lipids, waxes and the like and combinations thereof.

For example, the cap can be comprised of a polymeric material that is at least partially soluble in water. When such a cap is exposed to the aqueous environment of the lacrimal canaliculus or the tear fluid, it preferably will dissolve and release the active agent as it dissolves. The solubility in water of the material from which the cap is made typically will be directly proportional to its rate of dissolution. Suitable polymeric materials that are at least partially soluble in water include, for example: poly(ethylene glycol); poly(ethylene oxide); poly(propylene gycol); poly(vinyl alcohol); poly(hydroxyethyl methacrylate); poly(vinylpyrrolidone); polyacrylic acid; poly(ethyloxazoline); poly(dimethyl acrylamide); phosolipids, such as, for example, phosphoryl choline derivatives; polysulfobetains; polysaccharides and carbohydrates, such as, for example, hyaluronic acid, dextran, hydroxyethyl cellulose, hydroxyl propyl cellulose, gellan gum, guar gum, heparan sulfate, chondritin sulfate, heparin, and alginate; proteins such as, for example, gelatin, collagen, albumin, and ovalbumin; and polyamino acids. The polymeric materials in this list typically can be copolymerized or blended with hydrophobic polymers, monomers, or both.

Alternatively, the cap can be comprised of a biodegradable material that chemically degrades upon exposure to, for example, biologically active substances typically present in mammals. The biodegradable materials are preferably hydrolyzable under in vivo conditions. Biodegradation typically occurs more slowly than dissolution, and the cap can thus be made of biodegradable materials if slower, more sustained release of the active agent is desired. Suitable polymeric biodegradable materials include, without limitation, polymers and oligomers of glycolide, lactide, epsilon-caprolactone, and other hydroxy acids, and other biologically degradable polymers that yield materials that are non-toxic or present as normal metabolites in the body. Preferred poly(alpha-hydroxy acids) are poly(glycolic acid), poly(2-dioxanone); poly(DL-lactic acid) and poly(L-lactic acid). Other useful materials include poly(amino acids), polycarbonates, poly(anhydrides), poly(orthoesters), poly(phosphazines) and poly(phosphoesters). Polylactones such as poly(epsilon-caprolactone), poly(delta-caprolactone), poly(delta-valerolactone) and poly(gamma-butyrolactone), for example, are also useful, as are chitosan, alginates, collagen, and gelatin. In particular aspects of the invention, the polymeric material of which the caps are made can be a mixture of one or more dissolvable and bio-degradable polymers.

The cap can also be made of a material that is insoluble in water and non-biodegradable, but from which the active agent can diffuse. Suitable polymeric materials of this type include, for example, cross-liked polymers, such as, without limitation, cross-linked poly(ethylene glycol), poly(ethylene oxide), poly(propylene gycol), poly(vinyl alcohol), poly(hydroxethyl methacrylate), poly(vinylpyrrolidone), polyacrylic acid, poly(ethyloxazoline), and poly(dimethyl acrylamide). These polymers can be copolymerized or blended with one or both of hydrophobic polymers and monomers. Additional examples of suitable polymers that are insoluble in either or both water and non-biodegradable include, without limitation, silicones, polyurethanes, cyanoacrylates, polyacrylic acid, fibrin, and cross-linked proteins, such as, for example, albumin and collagen-gellatin.

Figure 10:
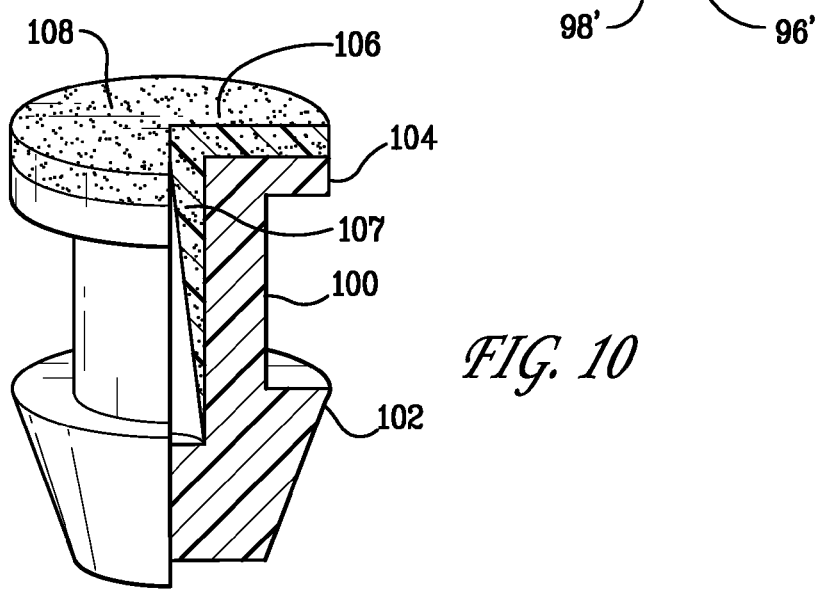
FIG. 10 is a three-dimensional view of the punctal plug depicted two-dimensionally in FIG. 8. The punctal plug has a body 100 with an enlarged segment 102, a collarette 104, and a cap 106 that includes a stem 107 and contains active agent 108. The stem portion 107 of the cap is clipped into the body 100 of the punctal plug.

In certain embodiments of the punctal plugs of the invention, the cap has a stem portion that is positioned within the body of the punctal plug. FIG. 10 is a three-dimensional view of a punctal plug body 100 having cap 106 affixed to collarette 104. Cap 106 has stem portion 107, which extends downwardly into body 100. The stem may be screwed or clipped, as shown in FIG. 10, into the body of the punctal plug, or is simply inserted into some portion of the body. Punctal plugs having caps with a stem portion may or may not have a collarette. The stem can be symmetrical or asymmetrical, depending upon the shape of the portion of the body into which it is inserted. The internal walls of the body may be substantially smooth or may include features that aid in maintaining the stem within the body including, without limitation, surfaces with grooves, indentations, roughness or the like in the interior walls. In an alternative embodiment, in addition to the active agent being disposed or dispersed throughout the cap, the active agent may be disposed on, dispersed throughout or otherwise contained in both the cap and the stem portion or in one of the cap or stem portion.

For those punctal plugs that have a collarette at the first end of the body, at least a portion of the cap is preferably adjacent to the collarette, and the active agent is preferably released into the tear fluid of the eye when the plugs are inserted into the lacrimal canaliculus. Punctal plugs that have a cap adjacent to the collarette can also have a cap at the second end of the body that faces the nasolacrimal duct when the punctal plugs are inserted into the lacrimal canaliculus, and the active agent is released from such punctal plugs into both the tear fluid of the eye and the nasolacrimal duct.

For certain punctal plugs, such as those having a collarette that are used to deliver active agent to the tear fluid of the eye, if the cap is made of a material that dissolves or erodes after insertion into the lacrimal canaliculus, a new cap can be added to the punctal plug, for example, after the cap dissolves or erodes, that contains active agent that is the same as or different from the active agent in the previous cap. The new cap may be made of a material that is the same as or different from the material of which the previous cap was comprised. The caps of certain punctal plugs can be replaced while the punctal plugs remain in the lacrimal canaliculus, while other punctal plugs are removed from the lacrimal canaliculus to replace the caps and are then reinserted into the lacrimal canaliculus. The caps of the punctal plugs can be replaced at any time after insertion into the lacrimal canaliculus, regardless of whether the caps have completely dissolved or degraded.

The active agent preferably passively diffuses from the caps of those punctal plugs that are made of p materials that are insoluble in water and non-biodegradable. Certain of such punctal plugs, such as those having a collarette that are used to deliver active agent to the tear fluid of the eye, have caps that can be removed from the punctal plugs, for example, after substantially all the active agent has diffused from the caps, and removal of the caps does not adversely affect the integrity of the remainder of the punctal plugs. New caps containing active agent that is the same as or different from the active agent in the previous caps can be added to the punctal plugs. The new cap can be comprised of a polymeric material that is the same as or different from the polymeric material of which the previous cap was comprised. The caps can be removed from some of such punctal plugs, and new caps can be added, after the punctal plugs have been inserted in the lacrimal canaliculus, and while the punctal plugs remain in the lacrimal canaliculus. Other punctal plugs are removed from the lacrimal canaliculus to replace the existing caps with new caps.

Certain of the punctal plugs that have collarettes can have a caps adjacent to the collarettes that are made of a flexible material. One or more portions of such caps can extend beyond the collarettes to increase the amount of active agent that the caps can hold. Suitable materials for such caps include, for example, low molecular weight polymers or elastomers such as, for example, polyolefins, polyesters, polyurethanes, acrylics, and copolymers thereof. In such punctal plugs, a portion of the cap rests against the collarette, and at least one portion of the cap preferably extends beyond the portion that rests against the collarette. In such punctal plugs, the caps can be transparent or flesh-colored.

Punctal plugs of the invention can be manufactured using processes that include techniques such as, for example, solution casting, extrusion, chemical cross-linking through the formation of covalent bonds or ionic bonds, lathing, compression molding, injection molding, liquid injection molding, blow molding, and polymerization, including photo polymerization, thermal polymerization, and ionic- and redox-initiated polymerization. The punctal plugs and caps are typically manufactured separately. The caps can be manufactured using processes that include techniques such as, for example, solution casting, extrusion, chemical cross-linking through the formation of covalent bonds or ionic bonds, lathing, compression molding, injection molding, liquid injection molding, blow molding, and polymerization, including photo polymerization, thermal polymerization, and ionic- and redox-initiated polymerization. The active agent can be incorporated into the caps by adding it to the materials that compose the caps during their manufacture through, for example, injection molding or dissolving the active agent into the cap material or the active agent can be added to the caps of the punctal plugs following their manufacture by, example and without limitation, soaking a solution of at least one active agent into a pre-formed cap as, for example, use of a solvent containing drug or covalently attaching the active agent following surface modification of the material.

The amount of active agent used in the plugs of the invention will depend upon the active agent or agents selected, the desired doses to be delivered via the punctual plug, the desired release rate, and the melting points of the active agent and material used to form the cap. Preferably, the amount used is a therapeutically effective amount meaning an amount effective to achieve the desired treatment, inhibitory, or prevention effect. Typically, amounts of about 0.05 to about 8,000 micrograms of active agents may be used.

The punctal plugs described herein can be used to deliver various active agents for the one or more of the treatment, inhibition, and prevention of numerous diseases and disorders. Each punctal plug can be used to deliver at least one active agent and can be used to deliver different types of active agents. For example, the punctal plugs can be used to deliver azelastine HCl, emadastine difumerate, epinastine HCl, ketotifen fumerate, levocabastine HCl, olopatadine HCl, pheniramine maleate, and antazoline phosphate for one or more of the treatment, inhibition, and prevention of allergies. The punctal plugs can be used to deliver mast cell stabilizers, such as, for example, cromolyn sodium, lodoxamide tromethamine, nedocromil sodium, and permirolast potassium.

The punctal plugs can be used to deliver mydriatics and cycloplegics, such as, for example, henylephrine, atropine sulfate, homatropine, scopolamine HBr, cyclopentolate HCl, tropicamide, and phenylephrine HCl. The punctal plugs can be used to deliver ophthalmic dyes such as, for example and without limitation, rose begal, sissamine green, indocyanine green, fluorexon, and fluorescein.

The punctal plugs can be used to deliver corticosteroids such as, for example, dexamethasone sodium phosphate, dexamethasone, fluoromethalone, fluoromethalone acetate, loteprednol etabonate, prednisolone acetate, prednisolone sodium phosphate, medrysone, rimexolone, and fluocinolone acetonide. The punctal plugs can be used to deliver non-steroidal anti-inflammatory agents such as, for example and without limitation, flurbiprofen sodium, suprofen, diclofenac sodium, ketorolac tromethamine, cyclosporine, rapamycin methotrexate, azathioprine, and bromocriptine.

The punctal plugs can be used to deliver anti-infective agents such as, for example and without limitation, tobramycin, moxifloxacin, ofloxacin, gatifloxacin, ciprofloxacin, gentamicin, sulfisoxazolone diolamine, sodium sulfacetamide, vancomycin, polymyxin B, amikacin, norfloxacin, levofloxacin, sulfisoxazole diolamine, sodium sulfacetamide tetracycline, doxycycline, dicloxacillin, cephalexin, amoxicillin/clavulante, ceftriaxone, cefixime, erythromycin, ofloxacin, azithromycin, gentamycin, sulfadiazine, and pyrimethamine.

The punctal plugs can be used to deliver agents for the one or more of the treatment, inhibition, and prevention of glaucoma including, without limitation, epinephrines, including, for example: dipivefrin; alpha-2 adrenergic receptors, including, for example, aproclonidine and brimonidine; betablockers, including, for example, betaxolol, cartcolol, levobunolol, metipranolol, and timolol; direct miotics, including, for example, carbachol and pilocarpine; cholinesterase inhibitors, including, for example, physostigmine and echothiophate; carbonic anhydrase inhibitors, including, for example, acetazolamide, brinzolamide, dorzolamide, and methazolamide; prostoglandins and prostamides, including, for example, latanoprost, bimatoprost, uravoprost, and unoprostone cidofovir.

The punctal plugs can be used to deliver antiviral agents, including, without limitation, fomivirsen sodium, foscarnet sodium, ganciclovir sodium, valganciclovir HCl, trifluridine, acyclovir, and famciclovir. The punctal plugs can be used to deliver local anesthetics, including, without limitation, tetracaine HCl, proparacaine HCl, proparacaine HCl and fluorescein sodium, benoxinate and fluorescein sodium, and benoxinate and fluorexon disodium. The punctal plugs can be used to deliver antifungal agents, including, for example, fluconazole, flucytosine, amphotericin B, itraconazole, and ketocaonazole.

The punctal plugs can be used to deliver analgesics including, without limitation, acetaminophen and codeine, acetaminophen and hydrocodone, acetaminophen, ketorolac, ibuprofen, and tramadol. The punctal plugs can be used to deliver vasoconstricors including, without limitation, ephedrine hydrochloride, naphazoline hydrochloride, phenylephrine hydrochloride, tetrahydrozoline hydrochloride, and oxymetazoline. Finally, the punctal plugs can be used to deliver vitamins, antioxidants, and nutraceuticals including, without limitation, vitamis A, D, and E, lutein, taurine, glutathione, zeaxanthin, fatty acids and the like.

The active agents delivered by the punctal plugs can be formulated to contain excipients including, without limitation, synthetic and natural polymers, including, for example, polyvinylalcohol, polyethyleneglycol, polyacrylic acid, hydroxymethyl cellulose, glycerine, hypromelos, polyvinylpyrrolidone, carbopol, propyleneglycol, hydroxypropyl guar, glucam-20, hydroxypropyl cellulose, sorbitol, dextrose, polysorbate, mannitol, dextran, modified polysaccharides and gums, phosolipids, and sulphobetains.

What is claimed is:

1. A punctal plug, the punctal plug comprising:
an elongated body having an enlarged segment on a first end and a collarette on a second end, the elongated body being configured for insertion into a lacrimal canaliculus of a patient;
a first cap affixed to and extending from an end of the enlarged segment, the first cap being configured as a carrier for one or more therapeutic agents for the controlled release therefor directly into the lacrimal canaliculus; and
a second cap affixed to the collarette, the second cap comprising a dome shaped top portion which extends over and covers the entire collarette, and a stem portion configured to extend into the elongated body, the second cap being configured as a carrier for one or more therapeutic agents for the controlled release therefor, wherein the stem portion is configured as a reservoir for additional therapeutic agent and supplies the additional therapeutic agent directly to the dome portion of the second cap, the dome shaped portion and the stem portion being formed from the same material, the dome shaped top portion of the second cap extends past the collarette for the release of the one or more therapeutic agents directly into the tear film on the eye.

2. A punctal plug, the punctal plug comprising:
an elongated body having an enlarged segment on a first end and a collarette on a second end, the elongated body configured for insertion into a lacrimal canaliculus of a patient; and
a cap affixed to the collarette, the cap comprising a dome shaped top portion which extends over and covers the entire collarette, and a stem portion configured to extend into the elongated body, the cap being configured as a carrier for one or more therapeutic agents for the controlled release therefore, wherein the stem portion is configured as a reservoir for additional therapeutic agent and supplies the additional therapeutic agent directly to the dome portion of the cap, the dome shaped portion and the stem portion being formed from the same material, the dome shaped top portion of the cap extends past the collarette for the release of the one or more therapeutic agents directly into the tear film on the eye.

* * * * *